United States Patent
Bicker et al.

(10) Patent No.: US 10,398,626 B2
(45) Date of Patent: Sep. 3, 2019

(54) CONTAINER WITH LOW PARTICULATE EMISSION AND FRICTION CONTROLLED DRY SLIDING SURFACE AND METHODS FOR PRODUCING SAME

(71) Applicant: Schott AG, Mainz (DE)

(72) Inventors: Matthias Bicker, Mainz (DE); Inka Henze, Nieder-Olm (DE); Joerg Schuhmacher, Kornwestheim (DE); Franziska Riethmueller, Frankfurt am Main (DE); Robert Hormes, Godach (CH); Christian Helbig, St. Gallen (CH); Marten Walther, Alfeld (DE); Manfred Lohmeyer, Nackenheim (DE)

(73) Assignee: SCHOTT AG, Mainz (DE)

( * ) Notice: Subject to any disclaimer, the term of this patent is extended or adjusted under 35 U.S.C. 154(b) by 576 days.

(21) Appl. No.: 14/250,494

(22) Filed: Apr. 11, 2014

(65) Prior Publication Data

US 2014/0305830 A1    Oct. 16, 2014

Related U.S. Application Data

(60) Provisional application No. 61/847,584, filed on Jul. 18, 2013.

(30) Foreign Application Priority Data

Apr. 11, 2013  (DE) ........................ 10 2013 103 676

(51) Int. Cl.

| | |
|---|---|
| *B32B 1/02* | (2006.01) |
| *A61M 1/00* | (2006.01) |
| *A61J 1/14* | (2006.01) |
| *B32B 1/08* | (2006.01) |
| *A61J 1/00* | (2006.01) |
| *A61M 3/00* | (2006.01) |
| *C03C 17/30* | (2006.01) |
| *C09D 183/08* | (2006.01) |
| *C09D 183/12* | (2006.01) |
| *A61J 1/05* | (2006.01) |
| *B65D 25/14* | (2006.01) |
| *C08G 77/24* | (2006.01) |

(52) U.S. Cl.
CPC .............. *A61J 1/1468* (2015.05); *A61J 1/00* (2013.01); *A61J 1/05* (2013.01); *A61M 1/0009* (2013.01); *A61M 3/00* (2013.01); *B32B 1/02* (2013.01); *B32B 1/08* (2013.01); *B65D 25/14* (2013.01); *C03C 17/30* (2013.01); *C09D 183/08* (2013.01); *C09D 183/12* (2013.01); *C08G 77/24* (2013.01)

(58) Field of Classification Search
CPC ..... B32B 1/00; B32B 1/02; B32B 1/08; A61J 1/00; A61J 1/05; A61J 1/14; A61J 1/1468; A61M 1/0009; A61M 3/00; C03C 17/30; Y10T 428/131; Y10T 428/1317; Y10T 428/1321; Y10T 428/1352; Y10T 428/1379; Y10T 428/1383; Y10T 428/139; Y10T 428/1393; Y10T 428/1397
See application file for complete search history.

(56) References Cited

U.S. PATENT DOCUMENTS

| | | | |
|---|---|---|---|
| 6,183,872 B1 | 2/2001 | Tanaka et al. | |
| 6,468,411 B1 * | 10/2002 | Eckles | C25D 3/565 205/246 |
| 8,124,207 B2 | 2/2012 | Sakhrani et al. | |
| 2009/0087646 A1 * | 4/2009 | Sirejacob | C03C 17/30 428/336 |
| 2011/0313363 A1 | 12/2011 | D Souza Ajit et al. | |

FOREIGN PATENT DOCUMENTS

| | | | |
|---|---|---|---|
| DE | 19921303 C1 | 10/2000 | |
| DE | 69832819 T2 | 9/2006 | |
| EP | 1391249 A1 | 2/2004 | |
| WO | WO02/30848 * | 4/2002 | ............ C04B 41/84 |
| WO | 2011060047 A1 | 5/2011 | |

OTHER PUBLICATIONS

European Search Report dated Sep. 30, 2014 corresponding to European Patent Application No. 14163381.8 with English translation, 10 pages.

German Office Action dated Nov. 21, 2013 corresponding to German Patent App. No. 10 2013 103 676.7 with English translation, 8 pp.

* cited by examiner

*Primary Examiner* — Walter Aughenbaugh
(74) *Attorney, Agent, or Firm* — Ohlandt, Greeley, Ruggiero & Perle, L.L.P.

(57) ABSTRACT

The invention relates to a container comprising a container body having an outer surface and an inner surface, wherein the inner surface contains silicon oxide; and the silicon oxide containing inner surface is at least partially modified with a fluorine containing compound, wherein the fluorine containing compound is chemically bonded to the silicon oxide of the container body via at least one Si—O—Si bond.

25 Claims, 9 Drawing Sheets

Normalized Pareto chart for contact angle to $H_2O$ after storage in $H_2O$ for 28 days

A: Pretreatment 550 °C, 30 min

D: Posttreatment duration

B: Posttreatment temperature

C: Relative humidity

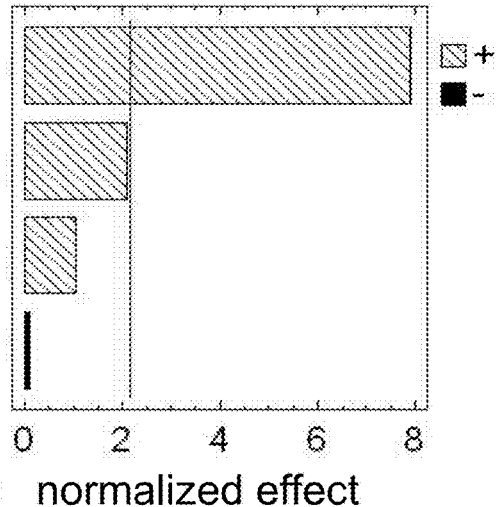

normalized effect

Fig. 8

Normalized Pareto chart for contact angle to $H_2O$ after storage in PBS for 28 days

A: Pretreatment 550 °C, 30 min

D: Posttreatment duration

C: Relative humidity

B: Posttreatment temperature

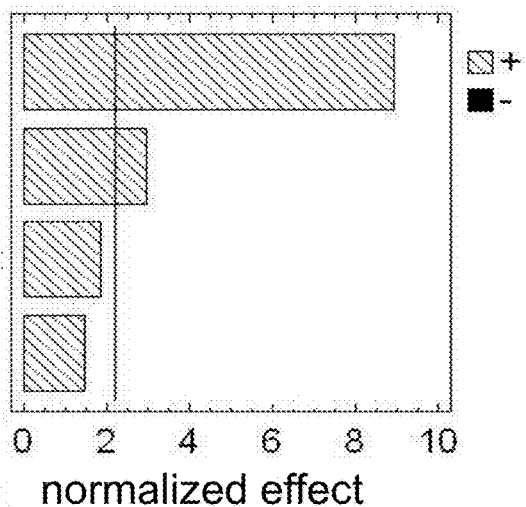

normalized effect

Fig. 9

CONTAINER WITH LOW PARTICULATE EMISSION AND FRICTION CONTROLLED DRY SLIDING SURFACE AND METHODS FOR PRODUCING SAME

The invention generally relates to containers and more particularly to containers that are part of a pharmaceutical packaging or of a medical device or a sterile packaging, such as syringe, cartridge or cannula systems and pharmaceutical vials.

In pharmaceutical packaging, such as syringe, cartridge or cannula systems and pharmaceutical vials, high demands are placed on the friction properties of the inner surface of the packaging. For example, the syringe plunger or the stopper of a vial should slide over the inner surface of the syringe or vial with the lowest possible friction. At the same time, as few particles or particle-forming substances or migratable lubricating oils as possible should be released from the inner surface of the packaging into the pharmaceutical contents, i.e. a pharmaceutical drug, in order to avoid contamination of the contents or an undesirable interaction of particles with the drug molecules or other components of the contents. For example, silicone oil-based particles have been known to be potential triggers of protein aggregation. Especially protein-based drug formulations may be very sensitive to contamination and interactions with particles. The term protein-based drug formulations refers to any liquid solutions that contain biomolecules, for example aqueous or alcoholic formulations. The biomolecules contained in the solution may include peptides, protein fragments, proteins, e.g. in particular specific species of proteins, such as monoclonal antibodies, polyclonal antibodies, ligands, receptors, antigens, enzymes, which have been produced naturally or recombinantly, and derivatives of these biomolecules.

Moreover, it is desired that the properties in terms of friction and particulate emission are maintained during long-term storage.

In order to obtain a silicone free syringe, it has already been proposed to coat the inner surface of the packaging with an alternative lubricating oil consisting of a fluorinated chemical compound. For example, U.S. Pat. No. 8,124,207 B2 proposes to apply lubricating oil including a perfluoropolyether (PFPE) or a functionalized perfluoropolyether to the surface of a pharmaceutical article. The surface provided with this lubricating oil is subjected to a flame plasma or an atmospheric plasma or to ionizing radiation or to an energy source at atmospheric pressure, and according to the teachings of this patent document it is in this way only that the desired sliding properties are obtained. That means, the desired sliding properties are only achieved by a very complex process using multi-stage process steps. Furthermore, what is suggested is not an oil-free solution, rather the silicone oil is merely replaced by another lubricating oil. Even after plasma curing, this perfluoropolyether-based lubricating oil includes free lubricating oil which can migrate into the drug solution, where it can lead to unwanted side effects. Moreover, particles might even be formed in conjunction with this method and the lubricating oil.

Further, U.S. Pat. No. 6,183,872 B1 and WO 2011/060047 A1 disclose the coating of surfaces with fluorinated chemical compounds to achieve antireflective and stain-resistant properties. Possible fields of application mentioned include the coating of optical elements (lenses, displays, etc.), inter alia.

In US 2011/0313363 A1 a medical article is described, which is initially provided with an organopolysiloxane-based layer. A second layer is applied by plasma-assisted CVD, which includes any of the following monomer groups: N-vinylpyrrolidone, vinyl acetate, ethylene oxide, alkyl acrylate, alkyl methacrylate, acrylamide, acrylic acid, and mixtures thereof. These layers reduce the breakaway force and the number of particles emitted by only a factor of about 13.4 as compared to silicone. Also, in US 2011/0313363 A1, the surface of the pharmaceutical packaging is provided with silicone oils to reduce the frictional force. However, a drawback thereof is that silicone oil molecules might migrate from the surface into the active substance solution stored in the packaging. That is because despite of overcoating the silicone with a second polymeric layer, silicone oil might be released from the layer system when subjected to mechanical or thermal stress, and may migrate into the product.

Therefore, an important object of the invention is to provide a container which exhibits reduced particulate emission from the inner surface of the container into the contents of the container as compared to the prior art.

Another object of the present invention is to provide a container which besides minimized particulate emission additionally exhibits improved friction properties at the inner surface and which can be manufactured cost-efficiently and with low complexity.

Another important object of the present invention is to provide a container in which additional lubricating oils such as silicone oils can substantially or entirely dispensed with.

Moreover, a container should be provided, which has a friction controlled surface of high storage stability, which is stable in interaction with the drug solution.

Another object of the present invention is to provide a container, whose properties in terms of friction and particulate emission are maintained during long-term storage.

These objects are achieved by a container and a method according to the independent claims. Advantageous embodiments and modifications are specified in the respective dependent claims.

According to the invention, a container is provided which comprises a container body with an outer surface and an inner surface, wherein the inner surface contains silicon oxide and the silicon oxide containing inner surface is modified with a fluorine containing compound, at least partially, wherein the fluorine containing compound is chemically bonded to the silicon oxide of the container body via at least one Si—O—Si bond. In particular, the chemical bond may be a chemical covalent bond.

In a preferred embodiment, the container is part of a pharmaceutical packaging or a medical device or a sterile packaging for storing a product, or of a sterile packaging for storing a pharmaceutical product.

The fluorine containing compound is an alkoxysilane compound of the following structure:

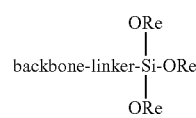

"ORe" represents an organic radical in form of an alkoxy group. The entity of the compound which is referred to as "backbone" contains fluorine.

The linker or linker entity enables the molecules of the fluorine containing compounds to form bonds with each other, i.e. crosslinks. This increases the stability of the compound and substantially reduces particulate emission from the modified inner surface of the pharmaceutical packaging according to the invention.

According to the invention, the alkoxysilane compound has one or more of the following features:
- the alkoxysilane compound contains a perfluoropolyether alkoxysilane as the backbone;
- the backbone comprises at least one $(CF_2)_3$ chain;
- the backbone comprises a plurality of $(CF_2)_x$ entities, and for all $(CF_2)_x$ entities x<8 is met;
- the backbone comprises $[(CF_2)_xO]_n$, with 3<n<1000, preferably 4<n<200, more preferably 5<n<100;
- the backbone comprises further branches in form of linear and/or branched and/or cyclic structures;
- the alkoxysilane compound comprises at least one $CF_3$ end group;
- the linker comprises at least one hydrolyzable group, and/or an amino group, and/or a carboxamide group —OC—NH—, and/or at least one further silane group, and/or an acrylate or methacrylate group, and/or an alkyl group —$C_xH_y$.

To ensure low particulate emission, the silicon oxide containing inner surface of the container, which is at least partially modified with a fluorine containing compound has a surface density of less than 2,000 particles/cm$^2$ for any particles of a diameter of ≥2 μm. Alternatively or additionally, in contact with an aqueous solution less than 10,000 particles of a diameter of ≥2 μm per ml solution volume will be released from the silicon oxide containing inner surface modified with a fluorine containing compound into the aqueous solution.

The container may further comprise an elastomeric stopper which is frictionally engaged with the inner surface of the container. In such an embodiment, the container is a syringe or a pharmaceutical cartridge, for example.

The modified inner surface of the container has one or more of the following features:
- the contact angle to water is greater than 100°, preferably greater than 105°, more preferably greater than 110°;
- the dynamic contact angle is greater than 110° upon immersion and greater than 90° upon retraction, preferably greater than 115° upon immersion and greater than 105° upon retraction;
- the roll-off angle is in a range from 1° to 30°, preferably in a range from 5° to 20°, as measured for a droplet of 60 μl;
- the inner surface is oleophobic and/or protein-repellent;
- the inner surface is oleophobic and hydrophobic.

In another embodiment, the modified container comprises a syringe or cartridge system comprising a plastic body made of cyclic olefin polymer (COP) or cyclic olefin copolymer (COC), and a glass-like inner coating, for example a silicon oxide containing intermediate layer to which the fluoroalkoxy silane compound is chemically bonded, at least partially, by forming an Si—O—Si bond. In a particular further embodiment, the coating comprises a further adhesion promoting layer which is directly coupled to the polymeric substrate of the syringe body.

Another feature of the container is that the friction reducing properties of the silicon oxide containing inner surface modified with a fluorine containing compound are maintained even after accelerated storage in water or phosphate buffer of pH 7 at storage conditions of 40° C. and 28 days.

Further, the container has at least one of the following material or substrate properties:
- the container is made of glass of hydrolytic class 1 or 2;
- the container is made of borosilicate glass;
- the container is a glass body with low particulate surface of less than 2,000 particles/cm$^2$ for any boron or tungsten or silicon containing particles of a diameter of ≥2 μm;
- the container is made of cyclic olefin polymer (COP) or cyclic olefin copolymer (COC);
- the container is a plastic body with a low particulate surface of less than 2,000 particles/cm$^2$ for any particles of diameters ≥2 μm;
- the container is a container body in form of a syringe body, cartridge body, or vial for medical purposes.

In another embodiment of the invention, the container comprises a container body which is modified with a fluorine containing compound only on a partial surface area $S_1$, with at least one of the following features:
- the container is not modified with a fluorine containing compound on at least one other partial surface area $S_2$;
- the container is not modified with a fluorine containing compound on two other spatially separated partial surface areas $S_2$ and $S_3$;
- in the area of at least one non-modified partial surface area the container is bonded to a different material;
- in the area of at least one non-modified partial surface area an adhesive material is applied.

For example, the adhesive material may be an adhesive, e.g. an adhesive for medical applications, for example an adhesive that is crosslinkable using electromagnetic radiation.

The invention also provides a method for producing a container exhibiting low particulate emission. This method comprises the steps of:
a) providing a container body having an outer surface and an inner surface, wherein the inner surface contains silicon oxide;
b) applying a mixture of an organic fluorine compound dissolved in a solvent to at least a portion of the inner surface of the container body;
c) drying the fluorine containing compound and crosslinking it with the silicon oxide containing inner surface of the container body by a condensation reaction.

Another feature of the method is that the fluorine containing compounds crosslink with each other.

The concentration of the organic fluorine compound used in step b) is in a range from 0.01% to 1%, preferably in a range from 0.03% to 0.5%, more preferably in a range from 0.05% to 0.3%.

In step b) a fluorine containing solvent may be used which contains at least one of the following compounds:
Ethoxynonafluorobutane;
Methoxynonafluorobutane;
Perfluorohexane;
Hydrofluoroether;
Solvay Solexis HAS-110;
Fluorinert FC-77;
Perfluorosolv PFS-1;
Perfluorosolv PFS-2.

The crosslinking may be accomplished under the direct effect of temperature and/or water, in particular in a wet gas atmosphere, or under the effect of an aqueous solution, in particular an acid solution.

The crosslinking is accomplished at a temperature above 30° C. or at a relative humidity in a range from 10% to 95%, more preferably in a range from 30% to 70%. For this purpose, the coated pharmaceutical packaging is placed in a climate cabinet in which the values of relative humidity and temperature can be preset.

Alternatively, it is also possible that crosslinking is accomplished in air, under the effect of atmospheric humidity from the environment.

In the step of providing the container body, the inner surface of the container may be pretreated, at least partially, wherein the pretreating is performed by at least one of the steps of:
- thermal pretreatment at a temperature above 350° C., preferably above 400° C., more preferably above 500° C.;
- washing with a sterile, low particulate water;
- wet-chemical pretreatment with an acidic or an alkaline solution;
- cleaning according to any of the two preceding steps using ultrasound at a frequency in a range from 20 kHz to 2.5 MHz, preferably at a frequency in a range from 100 kHz to 2 MHz;
- drying, preferably by blowing in air, or in a continuous furnace.

Between the steps of providing the container body and of applying a mixture, an intermediate layer may be applied in an additional step a1) upon at least a partial area of the inner surface of the container body, wherein the intermediate layer exhibits at least one of the following features;
- the intermediate layer functions as an adhesion promoting layer;
- the intermediate layer comprises silicon oxide;
- the intermediate layer is a sol-gel-based layer;
- the intermediate layer comprises at least one understoichiometric or over-stoichiometric oxide compound;
- the intermediate layer is doped with further compounds;
- the intermediate layer comprises a mixed oxide, preferably a doped silicon oxide, more preferably a silicon oxide doped with an oxide of elements Al, Mg, P, Ce, Zr, Ti, Ba, Sr, Nb, B, or with magnesium fluoride.

To further improve the properties of the coating, the inner surface of the container may additionally be posttreated after step c), at least partially, wherein the posttreatment is performed by at least one of the following steps:
- drying under ambient conditions or in a furnace;
- post-cleaning by means of an ultrasonic bath, and/or using a solvent, and/or using a fluorine-containing solvent, and/or using the same solvent as in step b), and/or using water, preferably water for injection (WFI).

The applying of the mixture may be accomplished by liquid coating, wherein the liquid coating is performed by any of the following methods:
- spray coating;
- dip coating;
- strike-off coating;
- wipe-on coating;
- flood coating;
- flow coating.

In the spray coating method, liquid coating is performed using a two-substance or a single-substance nozzle, preferably a diving nozzle (i.e. a nozzle which dives into the container during the spraying operation), or an ultrasonic atomizer.

The container of the invention is preferably used as a syringe system with friction controlled surface for storing pharmaceutical drug solutions, in particular protein-based and antibody-based pharmaceutical drug formulations.

The invention will now be described in more detail with reference to the accompanying drawings and by way of exemplary embodiments.

In the drawings:
FIG. 1 shows values of static and sliding friction for a glass syringe coated according to the invention;
FIG. 2 shows values of the contact angle to water for a glass syringe coated according to the invention;
FIG. 3 shows the breakaway force at the inner surface for a glass syringe coated according to the invention as a function of storage time and storage medium;
FIG. 4 shows the sliding friction force at the inner surface of a glass syringe coated according to the invention as a function of storage time and storage medium;
FIG. 5a shows particle concentration for a glass syringe coated according to the invention in comparison to a siliconized glass syringe and an uncoated glass syringe;
FIG. 5b shows an enlarged detail of FIG. 5a;
FIG. 6 shows the contact angle to water for a glass syringe coated according to the invention with and without thermal pretreatment;
FIG. 7 shows the sliding friction for a glass syringe coated according to the invention with and without thermal pretreatment;
FIG. 8 is a Pareto analysis of a statistical experimental design for target parameter "contact angle to water" after storage with water for 28 days at 40° C.;
FIG. 9 is a Pareto analysis of a statistical experimental design for target parameter "contact angle to water" after storage with a phosphate buffer for 28 days at 40° C.;
FIG. 10 is a Pareto analysis of a statistical experimental design for target parameter "sliding friction" after storage with water for 28 days at 40° C.;
FIG. 11 is a Pareto analysis of a statistical experimental design for target parameter "sliding friction" after storage with a phosphate buffer for 28 days at 40° C.;
FIG. 12 shows the sliding friction force for glass syringes coated according to the invention as a function of the coating method;
FIG. 13 shows the breakaway force for glass syringes coated according to the invention as a function of the coating method; and
FIG. 14 shows a force-distance chart of glass syringes coated with DC2634.

According to the invention a container is provided which in particular is a syringe system or cartridge system for storing and/or administering medical drugs in liquid form, or a pharmaceutical vial for storing such drugs. Such a container comprises a glass body having an outer surface and an inner surface, and the latter has an at least partially modified surface. The glass body comprises glass of hydrolytic class I or II.

Alternatively, the container may comprise a plastic body preferably based on cyclic olefin polymer (COP) or cyclic olefin copolymer (COC), which has an at least partially modified glass-like coating on its inner surface.

Further, the container comprises an elastomeric stopper which is frictionally engaged with the inner surface of the container. Moreover, the container may comprise a closure, such as an elastomeric tip cap.

The glass or glass-like surface has a content of silicon oxide of more than 50%, preferably of more than 60%, and more preferably of more than 65%.

The at least partial modification of the surface is accomplished using a fluorine containing compound which is chemically bonded to the silicon oxide containing inner surface via Si—O—Si bonds, at least partially. The fluorine containing compound applied to the surface is a monopodal fluorine containing alkoxysilane compound. Chemical bonding to the glass is effected by a condensation reaction.

An advantage of chemically binding the alkoxysilane compound as compared to a substance that is only spray-deposited, such as for example a spray-deposited perfluorinated polyether (PFPE) oil, is increased stability of the coating and enhanced connection to the substrate.

The alkoxysilane compound has the following basic structure:

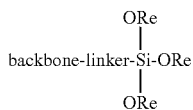

The abbreviation "ORe" designates an alkoxy group.

The alkoxysilane compound has at least one of the following features.

Because of the chemical bonding of the alkoxysilane to the surface, the backbone of the alkoxysilane compound is aligned towards the surface, with the result that the backbone remains movable thereby improving the friction properties of the surface.

The backbone contains fluorine. In particular, this backbone may include perfluoropolyether alkoxysilane.

Additionally, the fluorine containing backbone comprises at least one $(CF_2)_3$ chain, and optionally a plurality of $(CF_2)_x$ entities, for all of which x<8 applies.

Also, the fluorine containing backbone may comprise $[(CF_2)_xO]_n$, with 3<n<1000, preferably with 4<n<200, more preferably with 5<n<100.

The backbone may additionally include further branches. Moreover, it may include $CF_3$ groups as further branches, and/or linear, branched, and/or cyclic structures.

The backbone may be saturated or unsaturated.

The alkoxysilane compound may include at least one $CF_3$ end group.

Preferably, the alkoxysilane compound comprises a methoxysilane, so that the compound exhibits higher chemical reactivity when compared to an ethoxysilane, for example.

Between the backbone and the alkoxy silane group, a linker may be provided. The task of this linker is to crosslink two or more neighboring alkoxysilane containing molecules with each other, to thereby increase the stability of the coating applied to the surface.

The linker includes at least one of the following compounds:
  a hydrolyzable group;
  an amino group;
  a carboxamide group —OC—NH—;
  at least one further siloxane group;
  at least one further silane group;
  an acrylate or methacrylate group; or
  an alkyl group —$C_xH_y$.

An essential feature of the container or pharmaceutical packaging according to the invention is reduced contamination of the contents of the packaging due to minimized migration into and minimized interaction of components of the modified inner surface with the medical drugs. To avoid such contamination of the medical drugs, the modified inner surface is substantially free of fluid or mobile lubricating oils, at least until just before filling of the syringe or vial or before placing the stopper, so that it forms a dry sliding surface. The modified inner surface has not more than 5 $\mu g/cm^2$, preferably not more than 0.5 $\mu g/cm^2$, more preferably 0.005 $\mu g/cm^2$ mass of lubricating oil, normalized to 1 $cm^2$ of modified inner surface area.

Furthermore, the modified inner surface is substantially free of polyorganosiloxane compounds, such as silicone oils. This means that the surface does not include any polyorganosiloxane compounds, such as polydimethylsiloxane compounds (PDMS). The latter is defined by a maximum of 5 $\mu g/cm^2$, preferably a maximum of 0.5 $\mu g/cm^2$, more preferably 0.005 $\mu g/cm^2$ mass of such compounds, normalized to 1 $cm^2$ of modified inner surface area.

In a first refinement, the container body is completely free of polyorganosiloxane compounds on its entire inner surface. In a second refinement, the container is completely free of polyorganosiloxane compounds on those inner surface areas, which are in direct contact with the produce during storage.

In a third refinement, the container body is completely free of polyorganosiloxane compounds on both its inner and outer surfaces. In a fourth refinement, the entire container body is completely free of polyorganosiloxane compounds. In a fifth refinement, the entire container is completely free of polyorganosiloxane compounds.

The absence of silicone oils on the modified surface moreover reduces protein aggregation when compared to siliconized syringe bodies. A further advantage that may arise is reduced protein adsorption.

Furthermore, the alkoxysilane compound applied to the inner surface of the container or pharmaceutical packaging according to the invention is immobilized, at least substantially immobilized, and in particular is not able to migrate. This is defined by specifying that not more than 1%, preferably not more than 0.1%, more preferably not more than 0.01%, and most preferably a maximum of 10 ppm of the alkoxysilane compound is able to migrate from the surface into a solvent or into an aqueous solution. Further, when in contact with an aqueous solution having a volume V, not more than 1000 ppb, preferably not more than 500 ppb, and most preferably not more than 50 ppb of metal ions or metal oxide ions or metal containing particles, e.g. tungsten containing ions, will be released from the modified surface.

From particles formed during the manufacturing of glass, such as silicon oxide particles or borate or metal containing particles, not more them 10,000 particles per ml will be released from the modified surface, those particles having a diameter of ≥2 μm.

In summary, from a measurement that has been performed using a HYAC-Roco particle tester, the following distribution of the number of particles migrated into an aqueous solution resulted as a function of particle diameter:
  less than 10,000 particles of a diameter of ≥2 μm;
  less than 3,000 particles of a diameter of ≥5 μm;
  less than 100 particles of a diameter of ≥10 μm;
  less than 10 particles of a diameter of ≥25 μm; and
  less than 5 particles of a diameter of ≥50 μm.

Preferably, the following distribution of the number of particles migrated into an aqueous solution results:
  less than 1,000 particles of a diameter of ≥2 μm;
  less than 300 particles of a diameter of ≥5 μm;
  less than 50 particles of a diameter of ≥10 μm;
  less than 8 particles of a diameter of ≥25 μm; and
  less than 3 particles of a diameter of ≥50 μm.

Based on 1 ml of aqueous solution, the following distribution was measured:
  less than 300 particles/ml of a diameter of ≥2 μm;
  less than 70 particles/ml of a diameter of ≥5 μm,
  less than 30 particles/ml of a diameter of ≥10 μm;

less than 5 particles/ml of a diameter of ≥25 µm; and less than 2 particles/ml of a diameter of ≥50.

The friction properties of the modified surface will now be characterized by a comparison to the static and sliding friction forces resulting at a non-modified surface.

When compared to a non-modified surface, static and sliding friction is reduced by 1 N, preferably by 5 N. The variance of static and sliding friction is reduced by at least 0.5 N, preferably by at least 1 N.

In the unfilled state, i.e. dry, the modified surface exhibits a static friction below 20 N, preferably below 15 N, and more preferably below 15 N. Sliding friction is less than 10 N, preferably less than 8 N, and most preferably less than 4 N. The variance of static and sliding friction is less than ±4 N, preferably less than ±2 N, and more preferably less than ±1 N. These figures are also valid during the setting process of the stopper after filling.

In the "wet" state, i.e. when filled with water, the modified surface exhibits a static friction below 20 N, preferably below 15 N, and more preferably below 10 N. Sliding friction is less than 6 N, preferably less than 4 N, and more preferably less than 3 N. The variance of static and sliding friction is less than ±2 N, preferably less than ±1 N, and more preferably less than ±0.5 N. These figures are also valid during injection of the medical drug.

The specified values of resulting fractional forces were preferably measured using a FluroTec stopper Westar RU, B2-40, at a stroke speed of the plunger stopper of 100 mm/min, preferably with an Instron measuring system. The needles preferably used for this purpose were needles of size 27G×½" or size 29G×½".

Another potential source of contamination of the medical drug is that the stopper of the packaging is frictionally engaged with the modified inner surface, and therefore, when the stopper is moved along the surface, particles are released from the surface and migrate into and thereby contaminate the medical drugs.

The modified surface is distinguished by the feature that after one or more strokes of the elastomeric stopper frictionally engaged with the inner surface, not more than 2,000 particles per cm² surface area are released from the modified surface, those particles having a diameter of ≥2 µm. This feature is preferably measured using a scanning electron microscope.

If another friction partner is provided between the modified inner surface and the elastomeric stopper, for example an aqueous solution or a buffering solution, not more than 2,000 particles per cm² surface area are released from the modified surface, those particles having a diameter of ≥2 µm. This feature is preferably measured using a scanning electron microscope.

The thickness of the organic fluorine layer is in a range from 0.1 nm to 40 nm, preferably in a range from 0.5 nm to 10 nm, and more preferably in a range up to not more than 10 nm for a monolayer.

Another parameter of interaction between the surface modified according to the invention and water is the contact angle to water. For the coating of the invention, this angle is greater than 100°, preferably greater than 105°, and more preferably greater than 110°.

The dynamic contact angle of the layer surface is ≥110° upon immersion (advancing angle), preferably ≥115°, and is ≥115° upon retraction (receding angle), preferably ≥105°.

For a droplet of 60 µl volume, the roll-off angle of the layer is in a range from 1° to 30°, preferably in a range from 5° to 20°.

The glass body of the syringe comprises a cannula. When the inner surface of the cannula is not coated, adhesion of a needle glued to or staked in the cannula is increased. This is measured by a needle pull-off test in which the needle pull-off force is greater than 10 N, preferably greater than 22 N.

Since the outer surface of the container or pharmaceutical packaging is not coated, this increases the sticking strength of an adhesive label applied to the cater surface.

The invention also provides a method for producing a container that exhibits low particulate emission.

In a first step, a container body is provided having an outer surface and an inner surface. The inner surface contains silicon oxide.

Coating according to the invention is accomplished by applying a mixture of an organic fluorine compound dissolved in a solvent on at least a portion of the inner surface of the container body. The solvent used for this purpose contains fluorine and does not have a detrimental effect on ozone (zero ozone depletion potential).

The solvent or the diluted solution of the solvent and the organic fluorine compound have a boiling point in a range from 30° C. to 200° C., preferably in a range from 40° C. to 95° C., and more preferably in a range from 50° C. to 80° C.

The concentration of the organic fluorine compound in the solvent is in a range from 0.01% to 1%, preferably in a range from 0.03% to 0.5%, and more preferably in a range from 0.05% to 0.3%.

The solvent used for the method of the invention includes at least one of the following compounds:
Ethoxynonafluorobutane (3M Novec HFE7200, $C_4F_9OC_2H_5$);
Methoxynonafluorobutane (HFE-7100, $C_4F_3OCH_3$ consisting of the two isomers $(CF_3)_2CFCF_2OCH_3$ and $CF_3CF_2CF_2CF_2OCH_3$;
Perfluorohexane;
Hydrofluoroether;
Solvay Solexis HAS-110;
Fluorinert FC-77;
Perfluorosolv PFS-1; or
Perfluorosolv PFS-2.

In a further step, drying of the fluorine containing compound and crosslinking with the silicon oxide containing inner surface of the container body is accomplished by a condensation reaction.

Crosslinking of the layer is accomplished in a wet gas atmosphere or under direct exposure to water, to an aqueous solution, or in particular by being exposed to an acidic solution.

Relative humidity during the cross-linking of the layer is in a range from 10% to 95%, preferably in a range from 30% to 70%.

It is also possible to accomplish crosslinking of the layer by exposure to the atmospheric humidity from the environment.

During drying, in a temperature range between room temperature and 250° C., at least two volatile compounds will evaporate from of the layer.

Furthermore, crosslinking of the layer may be accomplished during a simultaneous sterilization process, e.g. ETO sterilization.

In one embodiment, the solution applied to the inner surface of the container or pharmaceutical packaging includes further additives or crosslinking agents, for example crosslinking agents which can be enabled by UV light or by heat.

In a further embodiment of the method, the glass or the glass-like surface of the container or pharmaceutical packaging may be pretreated prior to the actual coating. In this way, bound water or organic compounds may be removed from the glass surface.

For the pretreatment at least one of the methods described below is employed.

The glass is thermally pretreated at a temperature above 350° C., preferably above 400° C., and more preferably above 500° C.

The surface may be washed with sterile low particulate water.

The surface may be subjected to a wet-chemical pretreatment using an acidic or alkaline solution.

Additionally, the two latter pretreatment methods may be performed in an ultrasonic bath. The ultrasound employed has a frequency in a range from 20 kHz to 2.5 MHz, preferably in a range from 100 kHz to 2 MHz.

Following the pretreatment by any of the methods described above, drying of the surface is effected, preferably by blown-in air, or in a continuous furnace.

It could be demonstrated that such a pretreatment significantly increases the storage stability of the coating, which will be explained in more detail below, in conjunction with the description of exemplary embodiments.

The pretreatment of the glass or glass-like surface leads to a removal of the water skin and of organic substances on the surface, wherein the contact, angle to water prior to coating is less than 50°, preferably less than 20°.

In a further step of the inventive method, once the container has been provided, an intermediate layer is applied to the surface to enhance stability of the coating.

This intermediate layer may serve as an adhesion promoting layer. It may include silicon oxide. It is also possible that the intermediate layer is a sol-gel-based layer. Additionally or alternatively, the intermediate layer may include at least one under-stoichiometric or over-stoichiometric oxide compound. Moreover, this intermediate layer may be doped with further compounds.

In one preferred embodiment, the intermediate layer comprises a mixed oxide, preferably a doped silicon oxide. In a preferred embodiment, the silicon oxide is doped with an oxide of the following elements: aluminum, magnesium, phosphorus, cerium, zirconium, titanium, barium, strontium, niobium, boron. The silicon oxide may also be doped with magnesium fluoride.

In another embodiment of the inventive method, the coating is posttreated in a final step by post-cleaning the layer after it has been dried under ambient conditions or in a furnace.

This post-cleaning may be performed in an ultrasonic bath. In this case a solvent may be used which may include fluorine. The solvent may be the same as that -used for the coating. It is also possible to use water, e.g. water for injection (WFI), for the post-cleaning.

The actual deposition of the layer is accomplished by liquid coating. Techniques of liquid coating that may be employed include spray coating, dip coating, strike-off coating, wipe-on coating, flood coating, or flow coating.

In one preferred embodiment, spray coating is performed using a two-substance or a single-substance nozzle, e.g. an ultrasonic atomizer.

A homogeneous and local coating in the interior of a syringe is in particular achieved by using a diving nozzle.

The spray volume used for spray coating ranges from 0.1 µl to 500 µl, preferably from 3 µl to 150 µl, and more preferably from 20 µl to 100 µl.

When using a two-substance nozzle, the employed spray pressure ranges from 0.1 bar to 5 bar, preferably from 0.2 bar to 2.5 bar, and more preferably from 0.5 bar to 1.5 bar. The gas flow, when using a two-substance nozzle, is from 0.1 to 50 l/min, preferably from 0.5 to 20 l/min, and more preferably from 2 to 5 l/min.

The spray rate in the spraying process for applying the coating is from 0.01 µl/s to 100 µl/s, preferably from 25 µl/s to 100 µl/s. With the latter spray rate a spraying time from 0.5 s to 4 s will result.

Given the very short spraying time, high productivity is achieved in the production process according to the invention.

If a diving nozzle is employed, it will have an aperture diameter in a range from 0.1 mm to 1 mm.

The diving depth of the nozzle is in a range from 10% to 95%, preferably in a range from 30% to 90%, and more preferably in a range from 45% to 85% with respect to the height of the syringe or cartridge cylinder or to the height of the vial cylinder or of the ampoule.

The spray nozzle may be introduced into the interior of the pharmaceutical packaging to foe coated either vertically from above or from below, or horizontally.

For spray-coating a solution is used which has a kinematic viscosity, as measured at room temperature and atmospheric pressure, in a range from 0.01 to 10,000 centistokes, preferably in a range from 0.03 to 100 centistokes, more preferably in a range from 0.05 to 20 centistokes, and most preferably in a range from 0.1 to 2 centistokes.

In another embodiment of the method according to the invention, a staked needle syringe (i.e. a syringe with a glued-in needle) is coated by applying the coating only when the needle has already been introduced into the cannula. It has been found that with this approach, the glue bond of the needle and in particular the pull-off force of the needle are not adversely affected by spray-coating with the solution.

An syringe system coated according to the invention is used for storing pharmaceutical drug solutions, especially protein-based pharmaceutical drug formulations. By virtue of the inventive coating, protein adsorption, protein aggregation, and protein denaturation are reduced as compared to a conventional silicone containing syringe. This is especially true in the case that the pharmaceutical drug includes biomolecules that are intolerant or unstable to silicone oil.

According to the invention, the container described above may be used for storing a medical solution. In particular the container with modified glass surface may be used for storing solutions that include protein-based active substances and/or surfactants, such as polysorbate, e.g. Tween20 or Tween80, or Pluronics, and/or buffered or unbuffered drug solutions, and/or formulations with acidic or neutral or alkaline pH, and/or solutions of a formulation including sugar or sugar alcohol. Furthermore, the invention also comprises the use for storing drug solutions for example in pre-filled syringes or cartridges, e.g. in auto-injectors, or medical devices, which include medical drug solutions with the following ingredients: aqueous or alcoholic formulations, biomolecules, such as peptides, protein fragments, proteins, such as specific monoclonal antibodies, polyclonal antibodies, ligands, receptors, antigens, enzymes, which have been produced naturally or recombinantly, and derivatives of such biomolecules. Specific drug proteins include antibodies (e.g. Remicade and ReoPro from Centocor; Herceptin from Genentech; Mylotarg from Wyeth; Synagis from MedImmune), enzymes (e.g. Pulmozyme from Genentech; Cerezyme from Genzyme), recombinant hormones (e.g. Protropin from Genentech; Novolin from ZymoGenetics;

Humulin from Lilly), recombinant interferons (e.g. Actimmune from InterMune Pharmaceutical; Avonex from BiogenIdec; Betaseron from Chiron; Infergen from Amgen; Intron A from Schering-Plough; Roferon from Hoffman-La Roche), recombinant blood factors (e.g. TNKase from Genentech; Retavase from Centocor; ReFacto from Genetics Institute; Kogenate from Bayer), and recombinant erythropoietin (e.g. Epogen from Amgen; Procrit from J & J), and furthermore also recombinantly manufactured fusion proteins (e.g. Orencia/Abatacept from BMS), and vaccines (e.g. Engerix-B from GSK; Recombivax HB from Merck & Co.). Further, this layer may also be used for other biomolecular applications, e.g. nucleic acids, polynucleotides, such as DNA, RNA, pDNA, oligonucleotides, protein/nucleic acid complexes, and for iron-sucrose-containing formulation constituents, such as iron-sucrose complexes, and furthermore proteins with an amino-terminal γ-carboxyglutamic acid (Gla) domain with 9 to 12 Gla residues, such as a vitamin K-dependent coagulation zymogen protein or an activated form thereof, from the group comprising prothrombin. Factor VII, Factor IX, Factor X, and protein C, e.g. a recombinant human factor VII (Novo Nordisk).

Below, some embodiments of the container or pharmaceutical packaging of the invention will be described.

In a first embodiment, the pharmaceutical packaging of the invention is a glass syringe made of borosilicate glass. Such a glass is, for example, commercially available from the Applicant as pharmaceutical glass tubing under the trade name FIOLAX. The syringe is of the 1 ml long size and has a staked needle of the 27G×½" type.

The glass syringe is first cleaned with water for injection (WFI) and is then cleaned for 10 minutes in an ultrasonic bath using solvent HFE7200. For the subsequent coating of the inner surface of the syringe, one of the commercially available coatings Daikin AES4-E, Daikin DSX ("OPTOOL"), or Dow Corning 2634 is used. Each of these three coatings comprises a perfluoropolyether silane. By means of solvent HFE7200 the employed perfluoropolyether silane is diluted to a concentration of 0.1% and is stirred with a magnetic stirrer.

The interior of the glass syringe is flooded with the diluted solution. After a contact time of 3 minutes, excess coating solution is removed from the syringe. Then the syringe is dried in air, so that the solvent evaporates. In a next step, the coatings on the inner surfaces of the syringes are cured in a climate cabinet at a temperature of 50° C. and relative humidity of 50% for one hour. Finally, the syringes including the post-cured coating are post-cleaned in an ultrasonic bath using HFE7200.

FIG. 1 shows measured values of the breakaway force and gliding friction force, that were determined using a Flurotec Westar RU B2-40 stopper, both for unfilled syringes ("dry") and for syringes filled with water ("wet"), with a speed of 100 mm/min. A glass syringe with uncoated inner surface serves as a reference. The measurements were performed for each of the coatings mentioned above. The measurements indicate a significant reduction of the values of static and sliding friction. Also, the variance of these values is significantly reduced. For example, in the case of unfilled syringes, sliding friction was reduced to less than one-fifth of the reference value.

FIG. 2 shows measurements of the contact angle to water. In case of glass syringes with the inner surface coated, the contact angle to water is in a range from 115° to 120° for all of the three coatings, while it is only about 25° for the uncoated reference sample.

For the coatings Daikin DSX ("OPTOOL") and Dow Corning 2634, it was examined to what extent the friction values change as a function of storage period and storage medium of the syringes. For this purpose, a first number of the coated syringes and uncoated reference syringes was filled with water, and a second number with phosphate buffer of pH 7, and stored at a temperature of 40° C. in an accelerated test.

FIG. 3 shows the breakaway force of the samples as a function of storage time at a temperature of 40° C. and storage medium. For each of the two storage media, namely water and a phosphate buffer solution of pH 7 (PBS, pH 7), the breakaway force was measured before storage, after a storage period of 7 days, and after a storage period of 28 days. As can be seen from FIG. 3, a sustained reduction of the breakaway force of the filled syringes is achieved with the inventive coating.

FIG. 4 shows the sliding friction of the samples as a function of storage time and storage medium. The sliding friction was measured before storage with water, and for each of the two storage media (water and phosphate buffer) the sliding friction was measured in an accelerated test at a temperature of 40° C. after a storage period of 7 days and after a storage period of 28 days.

The measurements reveal a significant enhancement of storage stability of the syringe samples coated at the inner surface, both for water and for a phosphate buffer, when compared to an uncoated sample. FIG. 3 and FIG. 4 show that the low values of static and sliding friction of the coated syringe samples remain largely stable even over a long-term storage period.

In further measurements series, the glass syringes coated according to the invention with perfluoropolyether silane (Daikin DSX) were compared with glass syringes that were siliconized by spray-coating after a conventional manufacturing process with WFI.

FIG. 5a shows the number of particles in an aqueous solution for siliconized glass syringes and glass syringes coated with perfluoropolyether silane according to the invention. Uncoated syringes serve as a reference. FIG. 5a shows the entire measured distribution of particle sizes of the three syringes. FIG. 5b is an enlarged detail of FIG. 5a to make visible even the extremely low measured values of the syringe coated according to the invention.

The illustrated measurement results show that by coating the glass syringes with perfluoropolyether silane, a significant reduction of the invisible particles that are released into an aqueous solution is achieved, when compared to a siliconized syringe and an uncoated syringe. In particular, by virtue of the coating particulate emission of small invisible particles with diameters of ≤2 µm and ≤5 µm is reduced by more than a factor of 50.

Thus, the glass syringes coated according to the invention represent a significant improvement in terms of particulate emission over conventional siliconized syringes.

In a second exemplary embodiment, the pharmaceutical packaging according to the invention is again a glass syringe made of borosilicate glass. The syringe is of the 1 ml long size and has a staked needle of the 27G×½" type.

In a subsequent step, the syringes are thermally pretreated at 550° C. for 30 minutes, preferably under air.

For the subsequent coating of the inner surface of the syringe, the commercially available perfluoropolyether silane Daikin DSX ("OPTOOL") is used.

By means of solvent HFE7200, the employed perfluoropolyether silane is diluted to a concentration of 0.1% and is stirred with a magnetic stirrer.

The interior of the glass syringe is flooded with the diluted solution. After a contact time of 3 minutes, excess coating solution is removed from the syringe. Then, the syringe is dried in air, so that the solvent evaporates.

In a next step, the coatings on the inner surfaces of the syringes are cured in a climate cabinet at temperatures from 20° C. to 70° C. and a relative humidity from 30% to 90% for 0.5 to 72 hours, as a posttreatment.

Then, the syringes with the posttreated coating are post-cleaned in an ultrasonic bath using HFE7200.

With a statistical experimental design, a screening experimental design was performed using the parameters thermal pretreatment and the three posttreatment parameters temperature, relative humidity, and duration of posttreatment. Summary of Parameters Variations of Samples 1-9 and 10-18 of FIG. 6 and FIG. 7:

| sample # | T (° C.) | rel. humidity (%) | t (h) |
|---|---|---|---|
| 1 | 45 | 60 | 36.3 |
| 2 | 20 | 90 | 0.5 |
| 3 | 20 | 30 | 72 |
| 4 | 70 | 90 | 0.5 |
| 5 | 70 | 30 | 72 |
| 6 | 20 | 90 | 72 |
| 7 | 70 | 30 | 0.5 |
| 8 | 70 | 90 | 72 |
| 9 | 20 | 30 | 0.5 |
| 10 | 20 | 30 | 0.5 |
| 11 | 70 | 30 | 0.5 |
| 12 | 70 | 30 | 72 |
| 13 | 20 | 90 | 0.5 |
| 14 | 20 | 90 | 72 |
| 15 | 70 | 90 | 0.5 |
| 16 | 20 | 30 | 72 |
| 17 | 70 | 90 | 72 |
| 18 | 45 | 60 | 36.3 |

From the thermally pretreated and from the not thermally pretreated syringes, a first number of the samples was filled with water, and a second number with a phosphate buffer solution of pH 7 (PBS, pH 7), and stored in an accelerated test at a temperature of 60° C.

FIG. 6 shows results of measurements on these samples of the contact angle to water. The storage period was 28 days in each case.

Furthermore, sliding friction values of the pretreated and not pretreated glass syringes were measured and compared. The results of these measurements are shown in FIG. 7. Sliding friction was measured using a FluroTec Westar RU B2-40 stopper. The syringes were filled with water and phosphate buffer solution of pH 7, respectively, and stored as in the example of FIG. 6. The measurements were performed with a speed of 100 mm/min.

As can be seen from the measured values of FIG. 7, a thermal pretreatment of the glass syringes prior to being coated with a perfluoropolyether silane leads to a significant increase in the contact angle to water, even after storage in water or in a phosphate buffer. That means, the coatings on thermally pretreated glass syringes exhibit a much better storage stability when compared to similar coatings on glass syringes that had not been thermally pretreated.

Moreover, a thermal pretreatment of the glass syringes prior to being coated with a perfluoropolyether silane results in a significant reduction of the sliding friction values when compared to not thermally pretreated glass syringes, even after storage in water or phosphate buffer. This proves the enhanced stability of the coatings on thermally pretreated glass syringes. From the measured values shown in FIG. 7 it can be concluded that among the thermally pretreated glass syringes parameter variations 16 and 17 represent an optimum, since in these two cases sliding friction only slightly increases after having been stored.

These conclusions as to a substantial stability improvement of the coating are proved by the Pareto analyses of the statistical experimental design shown in FIGS. 8 and 9.

FIG. 8 shows the results of a Pareto analysis of the statistical experimental design for target parameter "contact angle to water" after a storage period of 28 days when filling the glass syringes with water at 60° C.

FIG. 9 shows the results of a Pareto analysis of the statistical experimental design for target parameter "contact angle to water" after a storage period of 28 days when filling the glass syringes with a phosphate buffer of pH 7 at 60° C.

FIGS. 8 and 9 show that a thermal pretreatment of the glass syringes prior to being created statistically significantly increases the contact angle to water measured after a storage period of 28 days with water or with a phosphate buffer at 60° C. when compared to glass syringes that were not thermally pretreated. FIGS. 8 and 9 furthermore show that the parameter "thermal pretreatment" is the stronger influencing factor when compared to posttreatment parameters temperature, relative humidity and duration of posttreatment.

Figure 1:
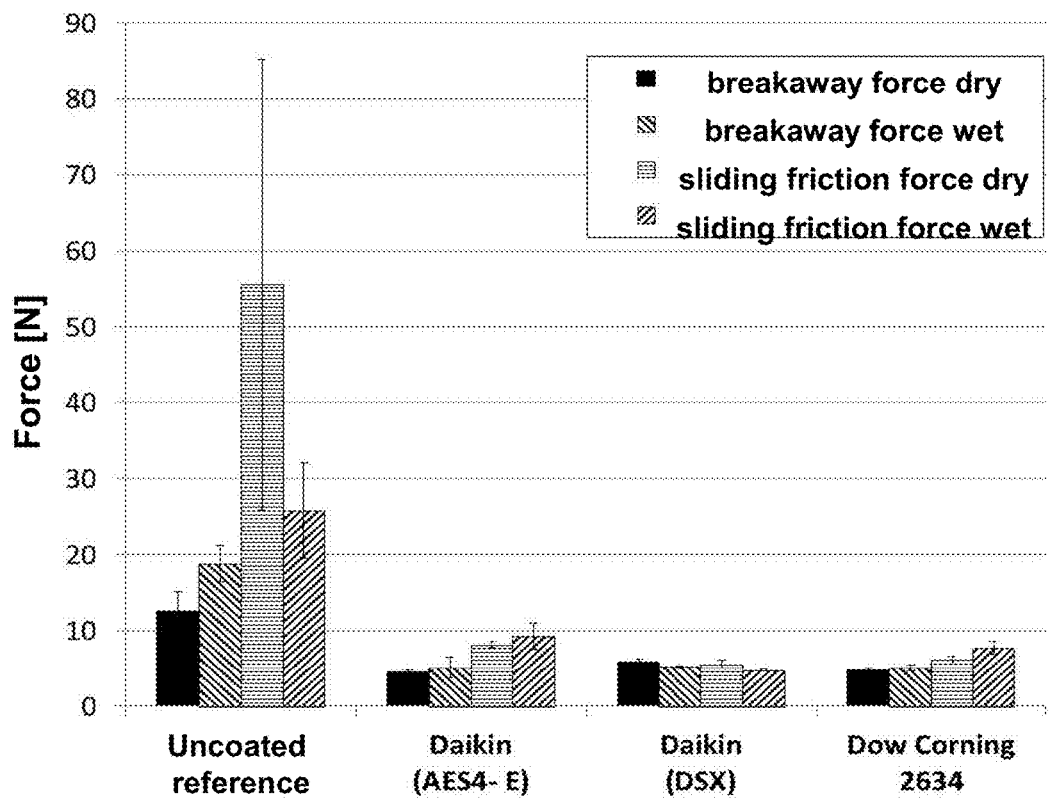
Figure 2:
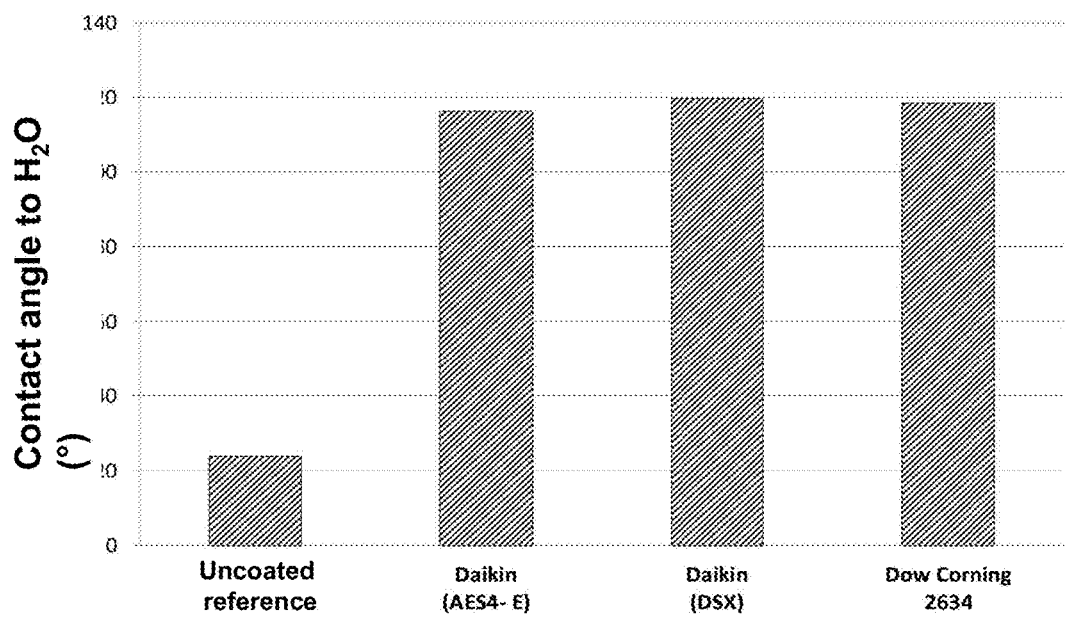
Figure 3:
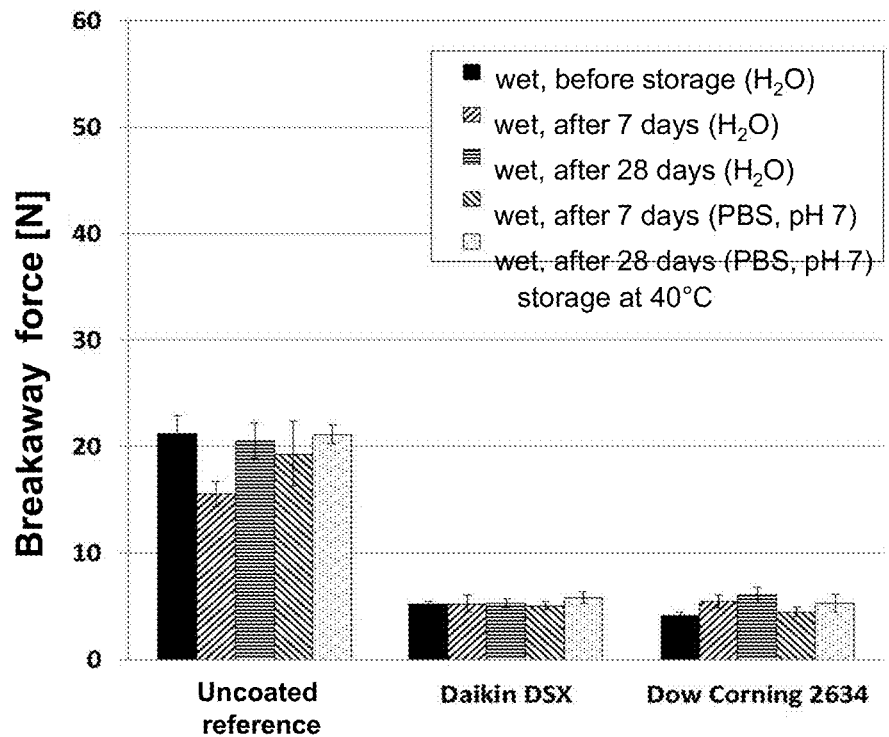
Figure 4:
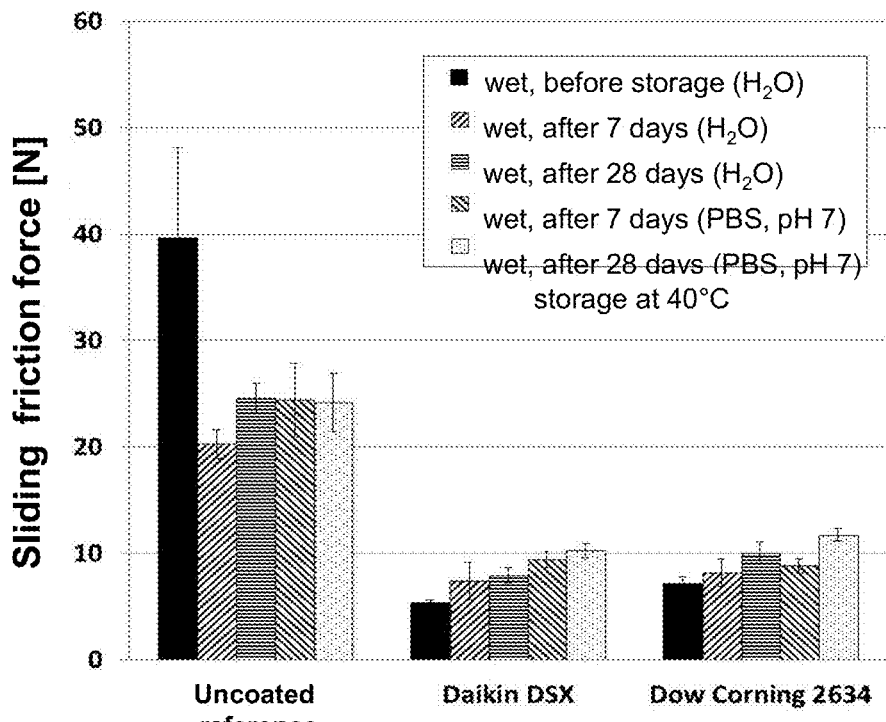
Figure 5A:
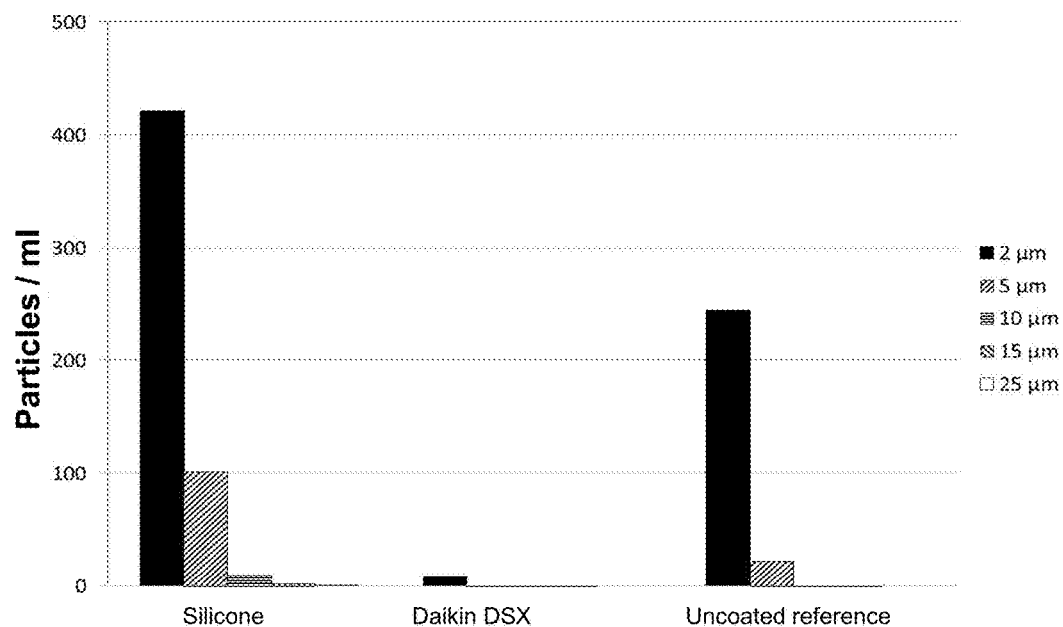
Figure 5B:
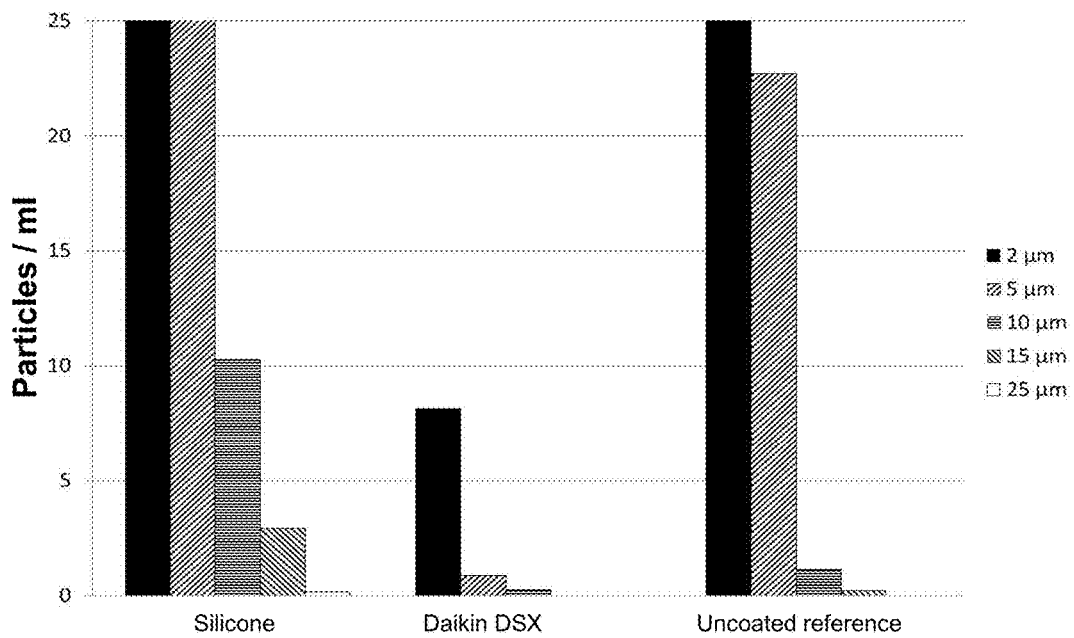
Figure 6:
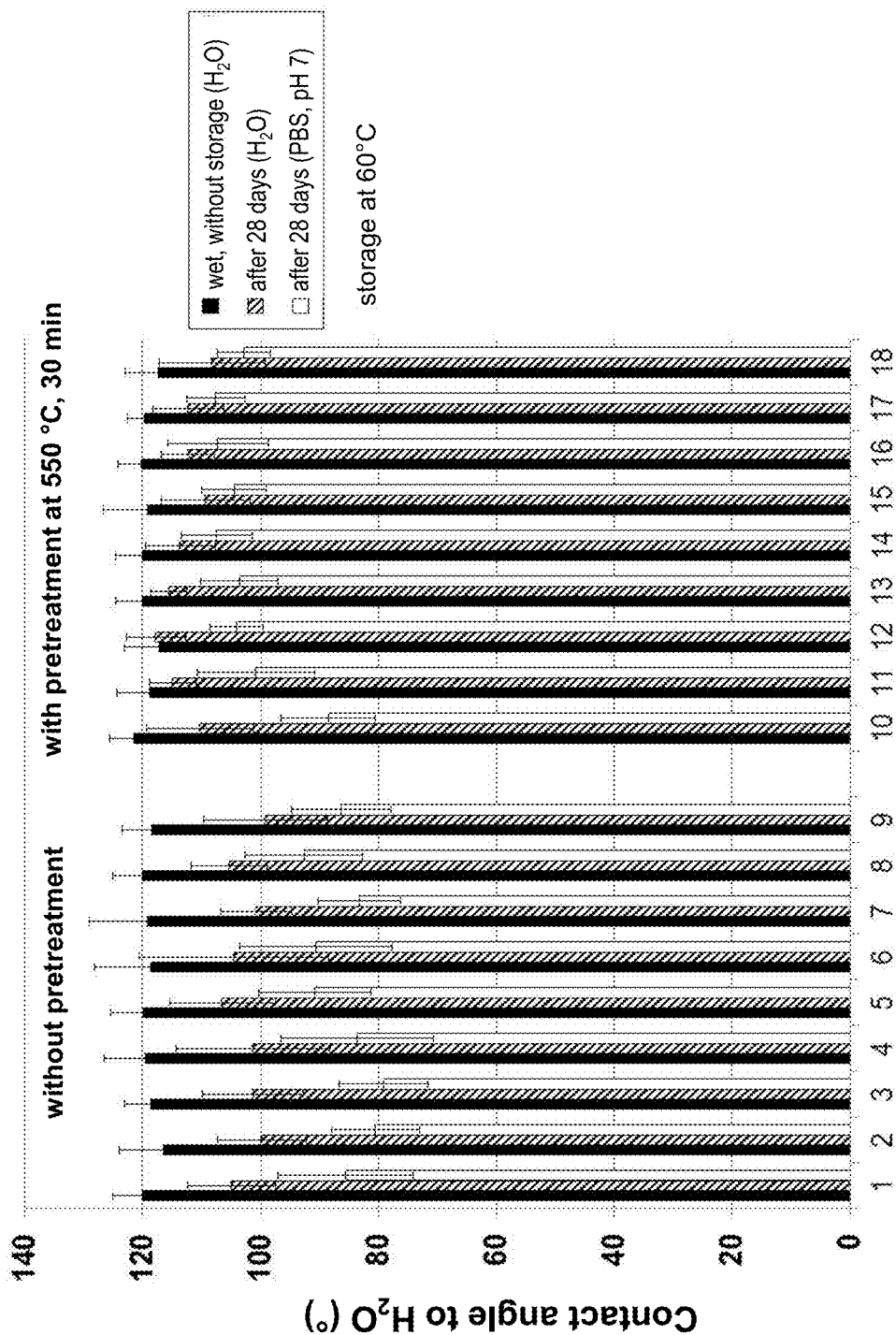
Figure 7:
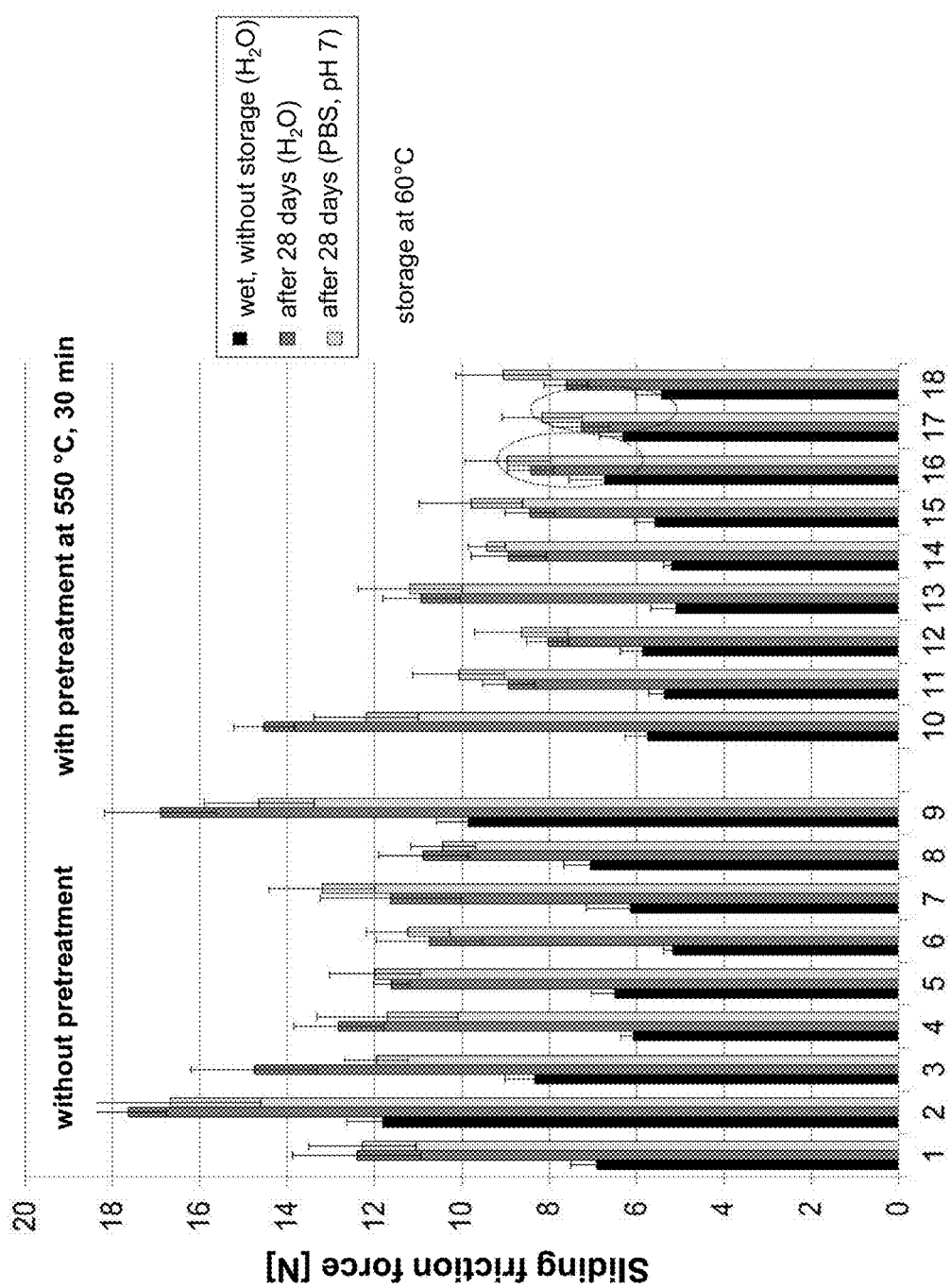
Figure 10:
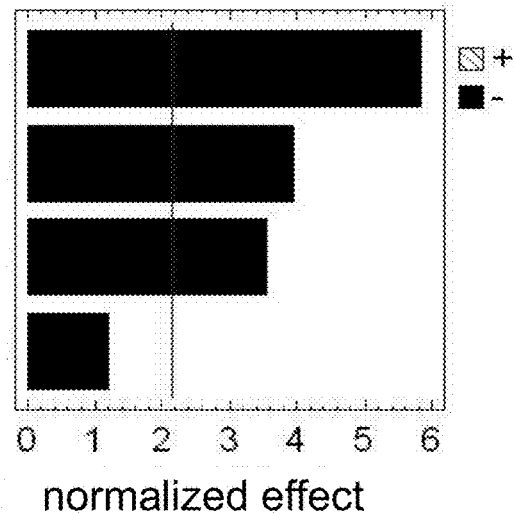

FIG. 10 shows the results of a Pareto analysis of the statistical experimental design for target parameter "sliding friction" after a storage period of 28 days when filling the glass syringes with water at 60° C.

Figure 11:
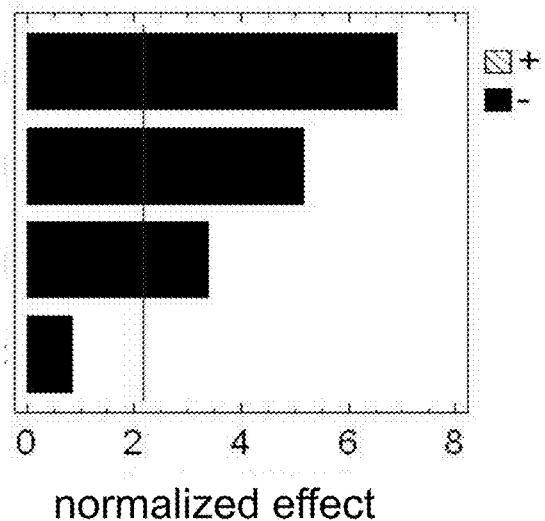

FIG. 11 shows the results of a Pareto analysis of the statistical experimental design for target parameter "sliding friction" after a storage period of 28 days when filling the glass syringes with a phosphate buffer of pH 7 at 60° C.

FIGS. 10 and 11 show that due to the thermal pretreatment of the glass syringes prior to being coated, the sliding friction after storage with water or with a phosphate buffer is statistically significantly lower than without thermal pretreatment. FIGS. 10 and 11 furthermore show that the parameter "thermal pretreatment" is the stronger influencing factor when compared to posttreatment parameters temperature, relative humidity and duration of posttreatment.

In a third exemplary embodiment, the pharmaceutical packaging of the invention is again a glass syringe made of borosilicate glass, e.g. of FIOLAX. Again, it is of the 1 ml long size with staked needle (27G×½"). First, the syringe is cleaned with WFI.

For the coating according to the invention, the perfluoropolyether silane Daikin DSX ("OPTOOL") is diluted to a concentration of 0.1% using solvent HFE7200, and is stirred with a magnetic stirrer.

Then, a two-substance nozzle (5 mm×90 mm, orifice diameter 0.25 mm) is introduced into the glass syringe from above, as a diving nozzle, over a travel distance of 40 mm. The inner surface of the glass syringe is spray-coated with the diluted solution in a dynamic spraying process. During this process, the spraying nozzle is retracted from the syringe body over the travel distance of 40 mm with a travel speed of 20 mm/s. The spraying volume is 50 µl. The spraying pressure is 0.5 bar, the gas flow is 2.8 l/min.

In a next step, the coating on the syringe is cured in a climate cabinet for a period of one hour, at a temperature of 50° C. and a relative humidity of 50%.

For the syringes coated in this manner, values of static and sliding friction were measured. For this purpose, a number of the syringes was filled with water and another number was filled with a phosphate buffer of pH 7 and stored in an accelerated test at a temperature of 40° C., for a period of 28 days. The values of static and sliding friction were measured using a FluroTec Westar RU B2-40 stopper.

Figure 12:
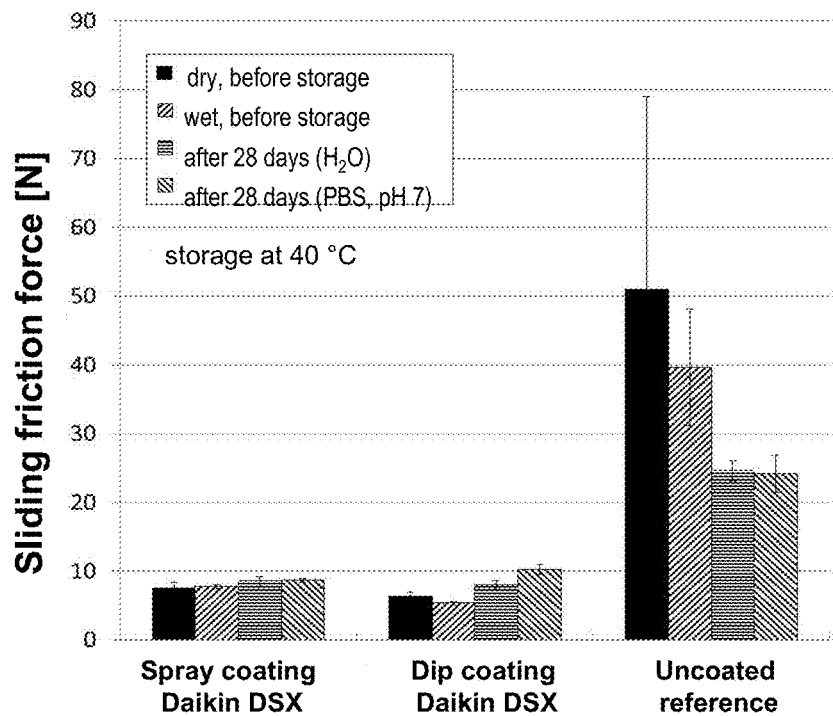

FIG. 12 shows the values of static and sliding friction for unfilled ("dry") and filled ("wet") syringes. A comparison was made between syringes in which the coating was applied by a spray coating method and syringes in which the coating was applied by a dip coating method according the first exemplary embodiment. Again, an uncoated syringe served as a reference.

Figure 13:
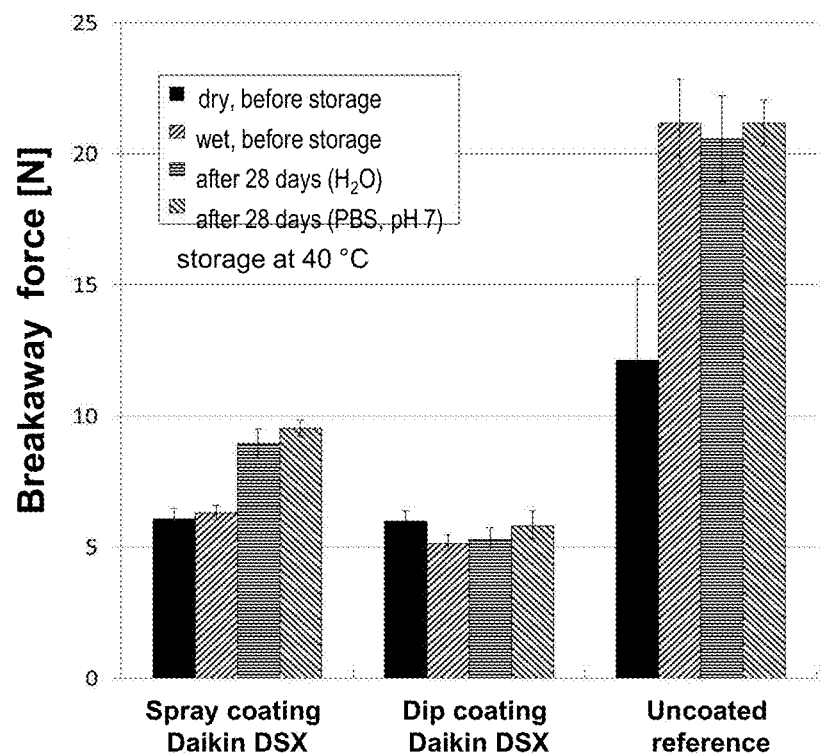

FIG. 13 shows the breakaway force for syringes of the same type as in FIG. 12.

FIGS. 12 and 13 show that the coated syringes exhibit significantly lower values of sliding friction force and breakaway force as compared to uncoated syringes. A significant dependency of this reduction of friction forces on the type of coating method, spray coating or dip coating, could not be determined. The extent of reduction is similar for both methods.

In a fourth exemplary embodiment, the glass syringes are coated using a two-substance nozzle, like in the third exemplary embodiment described above. However, in this case a perfluoropolyether silane containing mixture of type DC2634 was used.

Figure 14:
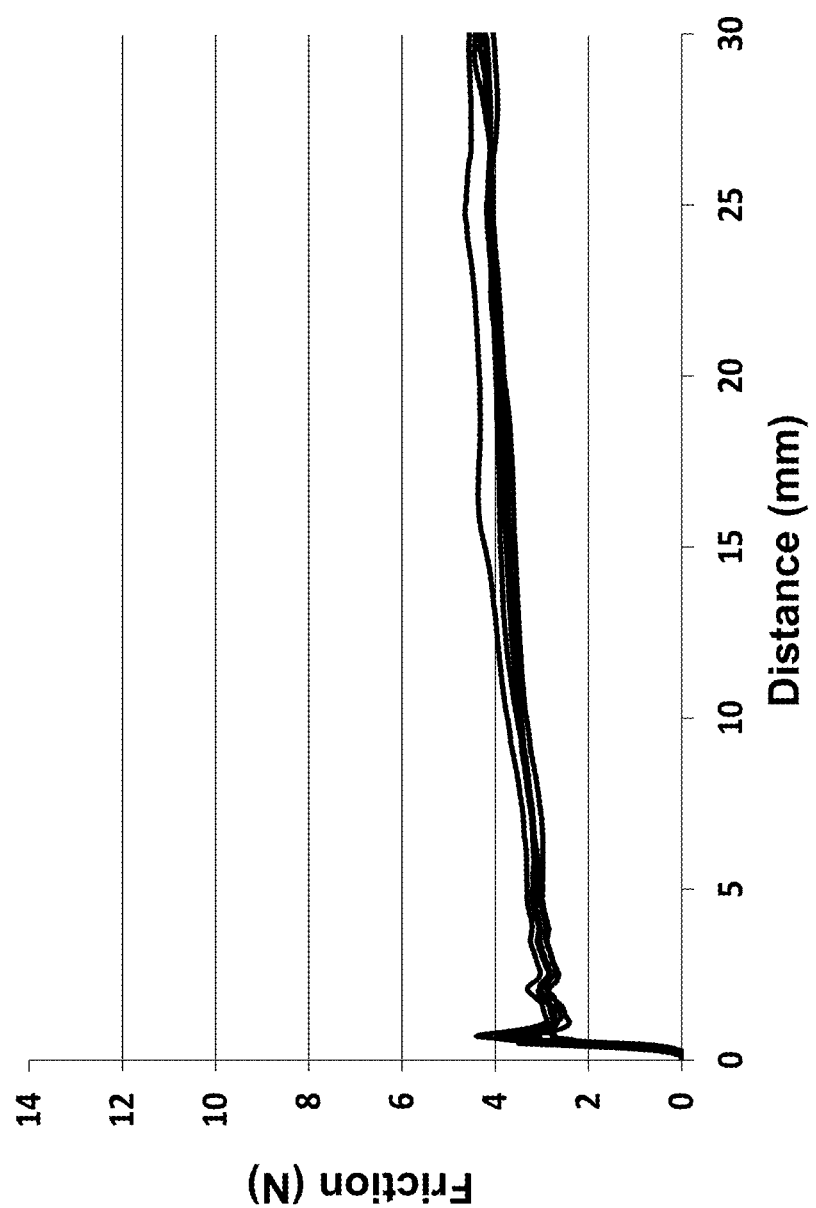

FIG. 14 shows the force-distance curve of glass syringes coated using DC2634. The measured values of static and sliding friction are very low, in a range around 4 N, at a speed of 100 mm/min.

In a fifth exemplary embodiment, the pharmaceutical packaging of the invention is a pharmaceutical vial. It is first cleaned using WFI and then coated by a process as follows.

As a perfluoropolyether silane, Daikin DSX ("OPTOOL") is diluted to a concentration of 0.1% using solvent HFE7200, and is stirred with a magnetic stirrer. The interior of the vial is flooded with the diluted solution.

After a contact time of three minutes, excessive coating solution is removed from the vial. Subsequently the vials are dried in air, so that the solvent evaporates. In a next step, the coatings on the inner surface of the vials are cured in a climate cabinet for a duration of one hour, at a temperature of 50° C. and a relative humidity of 50%. Then, the vials with the post-cured coating are post-cleaned in an ultrasonic bath using HFE7200.

The pharmaceutical vials coated in this manner according to the invention had protein-repelling layers with a contact angle in a range from 115° to 125°.

In a sixth exemplary embodiment, the pharmaceutical packaging according to the invention is again a pharmaceutical vials. It is first cleaned using WFI and then coated by a process as follows.

As a perfluoropolyether silane, Daikin DSX ("OPTOOL") is diluted to a concentration of 0.1% using solvent HFE7200, and is stirred with a magnetic stirrer.

The vial is immersed in the diluted solution and is thereby coated on its outer surface. After a holding time of three minutes, the vial is retracted from the solution and then dried in air, so that the solvent evaporates.

In a next step, the vials are cured in a climate cabinet for a duration of one hour, at a temperature of 50° C. and a relative humidity of 50%. Then, the vials with the post-cured coating are post-cleaned in an ultrasonic bath using HFE7200.

Measurements showed that the vials coated according to the invention exhibited significantly reduced particulate emission, friction-reducing properties, and a contact angle in a range from 115° to 120°.

In a seventh exemplary embodiment, the pharmaceutical packaging according to the invention is again a pharmaceutical vial. It is first cleaned using WFI and then coated by a process as follows.

As a perfluoropolyether silane, Daikin DSX ("OPTOOL") is diluted to a concentration of 0.1% using solvent HFE7200, and is stirred with a magnetic stirrer.

A diving nozzle (5 mm×90 mm, orifice diameter 0.25 mm) is introduced into the vial. The inner surface of the vial is spray-coated with the diluted solution, while the spraying nozzle is retracted from the vial body. In a next step, the coating on the vial is cured in a climate cabinet for a duration of one hour, at a temperature of 50° C. and a relative humidity of 50%.

A result of the inventive coating for the pharmaceutical vials are protein-repellent layers with a contact angle in a range from 115° to 125°.

In an eighth exemplary embodiment, the pharmaceutical packaging is a plastic syringe of cyclic olefin copolymer (COC) of size 50 ml. This plastic syringe has a glass-like, i.e. silicon oxide containing, coating on its inner surface. The syringe is first cleaned using WFI, and is then coated by the method as follows.

As the perfluoropolyether silane, Daikin DSX ("OPTOOL") is diluted to a concentration of 0.1% using solvent HFE7200, and is stirred with a magnetic stirrer.

The interior of the syringe is flooded with the diluted solution. After a contact time of three minutes, the syringe is removed from the solution and is then dried in air, so that the solvent evaporates.

In a next step, the coatings on the syringes are cured in a climate cabinet for a duration of one hour, at a temperature of 50° C. and a relative humidity of 50%. Then, the syringes with the post-cured coating are post-cleaned in an ultrasonic bath using HFE7200.

Measurements showed that the syringes coated according to the invention exhibited significantly reduced particulate emission, improved values of static and sliding friction, and a contact angle in a range from 115° to 120°.

In a ninth exemplary embodiment, the coatings were prepared similarly to the previous exemplary embodiments, however, pre-cleaning of the glass substrate with a solvent was dispensed with. In this case similarly good results were achieved, so that the manufacturing process may be significantly simplified.

In a tenth exemplary embodiment, the coatings were prepared similarly to the previous exemplary embodiments, however, post-cleaning of the coatings with a solvent was dispensed with. In this case similarly good results were achieved, so that the manufacturing process may be significantly simplified.

In an eleventh exemplary embodiment, the coatings were prepared similarly to the previous exemplary embodiments, however, pre-cleaning of the substrates and post-cleaning of the coated substrates were dispensed with. In this case similarly good results were achieved, so that the manufacturing process may be significantly simplified.

In a twelfth exemplary embodiment, the coatings were prepared similarly to the previous exemplary embodiments, however, post-curing and a wet climate were dispensed with. In this case similarly good results were achieved, so that the manufacturing process may be significantly simplified.

What is claimed is:

1. A container comprising a container body with an outer surface and an inner surface, wherein the inner surface comprises silicon oxide and is at least partially modified with a fluorine containing compound to provide a modified inner surface, wherein the fluorine containing compound is chemically bonded to the silicon oxide via at least one Si—O—Si bond,
wherein the fluorine containing compound is an alkoxysilane compound, the alkoxysilane compound having a structure as follows:

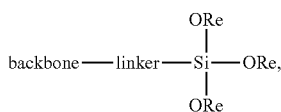

wherein ORe represents an alkoxy group,
wherein the backbone comprises a fluorine containing entity,
wherein the linker includes a functional group selected from the group consisting of at least one of a hydrolyzable group, an amino group, at least one further silane group, an acrylate, and a methacrylate group,
wherein the linker forms bonds between molecules of the alkoxysilane compound,
wherein the linker forms crosslinks between linkers of two or more neighboring fluorine containing compounds in a condensation reaction,
wherein the modified inner surface forms only a partial surface area of the inner surface such that at least one unmodified partial surface remains, and
wherein the at least one unmodified partial surface is bonded to a different material or has an adhesive material is applied.

2. The container as claimed in claim 1, wherein the container body is a part selected from the group consisting of: a pharmaceutical packaging; a medical device; and a sterile packaging for storing a product.

3. The container as claimed in claim 1, wherein the alkoxysilane compound has at least one further feature selected from the group consisting of: the alkoxysilane compound comprising a perfluoropolyether as the backbone; the backbone comprising at least one $(CF_2)_3$ chain; the backbone comprising a plurality of $(CF_2)_x$ entities, for all of which x<8 is met; the backbone comprising $[(CF_2)_xO]_n$, with 3<n<1000; the backbone comprising further branches in form of linear structures; the backbone comprising further branches in form of branched structures; the backbone comprising further branches in form of cyclic structures; the alkoxysilane compound comprising at least one $CF_3$ end group; and combinations thereof.

4. The container as claimed in claim 1, wherein the modified inner surface has a surface density of less than 2,000 particles/cm$^2$ for any particles of a diameter of ≥2 μm, or wherein in contact with an aqueous solution less than 10,000 particles of a diameter of ≥2 μm per ml of the aqueous solution are released from the modified inner surface into the aqueous solution.

5. The container as claimed in claim 1, further comprising an elastomeric stopper which is frictionally engaged with the modified inner surface.

6. The container as claimed in claim 1, wherein the modified inner surface is free of lubricating oils.

7. The container as claimed in claim 1, wherein the modified inner surface is free of polyorganosiloxane compounds with not more than 5 μg/cm$^2$ of such compounds normalized to 1 cm$^2$ of the modified inner surface.

8. The container as claimed in claim 1, wherein the modified inner surface has at least one feature selected from the group consisting of: a contact angle to water that is greater than 100°; a contact angle to water that is greater than 105°, a contact angle to water that is greater than 110°; a dynamic contact angle that is greater than 110° upon immersion and greater than 90° upon retraction; a dynamic contact angle that is greater than 115° upon immersion and greater than 105° upon retraction; a roll-off angle that is in a range from 1° to 30° as measured for a droplet of 60 μl; a roll-off angle that is in a range from 5° to 20° as measured for a droplet of 60 μl; oleophobic-repellent; protein-repellent; oleophobic; and hydrophobic.

9. The container as claimed in claim 1, wherein the modified inner surface has friction reducing properties that are maintained even after accelerated storage in water or phosphate buffer of pH 7 at storage conditions of 40° C. and 28 days.

10. The container as claimed in claim 1, further comprising at least one material or substrate property selected from the group consisting of: the container body being made of glass of hydrolytic class 1 or 2; the container body being made of borosilicate glass; the container body being made of glass with low particulate surface of less than 2,000 particles/cm$^2$ for any boron or tungsten or silicon containing particles of a diameter of ≥2 μm; the container body being made of cyclic olefin polymer (COP); the container body being made of cyclic olefin copolymer (COC); the container body being made of plastic with low particulate surface of less than 2,000 particles/cm$^2$ for any particles of diameters ≥2 μm; the container body being in the form of a syringe body; the container body being in the form of a cartridge body; and the container body being in the form of a medical vial.

11. The use of the container as claimed in claim 1 as a device selected from the group consisting of: a syringe system; a cartridge system; a medical device with low particulate emission; a medical device with a friction controlled surface for storing pharmaceutical drug solutions; and a medical device with a friction controlled surface for storing protein-based pharmaceutical drug formulations.

12. A container comprising a container body with an outer surface and an inner surface, wherein the inner surface comprises silicon oxide and is at least partially modified with a fluorine containing compound to provide a modified inner surface, wherein the fluorine containing compound is chemically bonded to the silicon oxide via at least one Si—O—Si bond, wherein the modified inner surface forms only a partial surface area of the inner surface such that at least one unmodified partial surface remains, and wherein the at least one unmodified partial surface is bonded to a different material or has an adhesive material is applied.

13. The container as claimed in claim 12, wherein the container body is a part selected from the group consisting of: a pharmaceutical packaging; a medical device; and a sterile packaging for storing a product.

14. The container as claimed in claim 12, wherein the fluorine containing compound is an alkoxysilane compound, the alkoxysilane compound having a structure as follows:

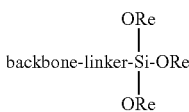

wherein ORe represents an alkoxy group, and wherein the backbone comprises a fluorine containing entity.

15. The container as claimed in claim 14, wherein the alkoxysilane compound has at least one feature selected from the group consisting of: the alkoxysilane compound comprising a perfluoropolyether as the backbone; the backbone comprising at least one $(CF_2)_3$ chain; the backbone comprising a plurality of $(CF_2)_x$ entities, for all of which x<8 is met; the backbone comprising $[(CF_2)_xO]_n$, with 3<n<1000; the backbone comprising further branches in form of linear structures; the backbone comprising further branches in form of branched structures; the backbone comprising further branches in form of cyclic structures; the alkoxysilane compound comprising at least one $CF_3$ end group; the linker comprising a hydrolyzable group; the linker comprising an amino group; the linker comprising a carboxamide group —OC—NH—; the linker comprising at least one further silane group; the linker comprising an acrylate; the linker comprising a methacrylate group; and combinations thereof.

16. The container as claimed in claim 12, wherein the modified inner surface has a surface density of less than 2,000 particles/cm² for any particles of a diameter of ≥2 μm, or wherein in contact with an aqueous solution less than 10,000 particles of a diameter of ≥2 μm per ml of the aqueous solution are released from the modified inner surface into the aqueous solution.

17. The container as claimed in claim 12, further comprising an elastomeric stopper which is frictionally engaged with the modified inner surface.

18. The container as claimed in claim 12, wherein the modified inner surface is free of lubricating oils.

19. The container as claimed in claim 12, wherein the modified inner surface is free of polyorganosiloxane compounds with not more than 5 μg/cm² of such compounds normalized to 1 cm² of the modified inner surface.

20. The container as claimed in claim 12, wherein the modified inner surface has at least one feature selected from the group consisting of: a contact angle to water that is greater than 100°; a contact angle to water that is greater than 105°, a contact angle to water that is greater than 110°; a dynamic contact angle that is greater than 110° upon immersion and greater than 90° upon retraction; a dynamic contact angle that is greater than 115° upon immersion and greater than 105° upon retraction; a roll-off angle that is in a range from 1° to 30° as measured for a droplet of 60 μl; a roll-off angle that is in a range from 5° to 20° as measured for a droplet of 60 μl; oleophobic-repellent; protein-repellent; oleophobic; and hydrophobic.

21. The container as claimed in claim 12, wherein the modified inner surface has friction reducing properties that are maintained even after accelerated storage in water or phosphate buffer of pH 7 at storage conditions of 40° C. and 28 days.

22. The container as claimed in claim 12, further comprising at least one material or substrate property selected from the group consisting of: the container body being made of glass of hydrolytic class 1 or 2; the container body being made of borosilicate glass; the container body being made of glass with low particulate surface of less than 2,000 particles/cm² for any boron or tungsten or silicon containing particles of a diameter of ≥2 μm; the container body being made of cyclic olefin polymer (COP); the container body being made of cyclic olefin copolymer (COC); the container body being made of plastic with low particulate surface of less than 2,000 particles/cm² for any particles of diameters ≥2 μm; the container body being in the form of a syringe body; the container body being in the form of a cartridge body; and the container body being in the form of a medical vial.

23. The use of the container as claimed in claim 12 as a device selected from the group consisting of: a syringe system; a cartridge system; a medical device with low particulate emission; a medical device with a friction controlled surface for storing pharmaceutical drug solutions; and a medical device with a friction controlled surface for storing protein-based pharmaceutical drug formulations.

24. The container as claimed in claim 14, wherein the linker forms bonds between molecules of the alkoxysilane compound.

25. A container comprising a container body with an outer surface and an inner surface, wherein the inner surface comprises silicon oxide and is at least partially modified with a fluorine containing compound to provide a modified inner surface, wherein the fluorine containing compound is chemically bonded to the silicon oxide via at least one Si—O—Si bond, wherein the fluorine containing compound is an alkoxysilane compound, the alkoxysilane compound having a structure as follows:

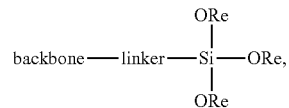

wherein ORe represents an alkoxy group, wherein the backbone comprises a fluorine containing entity, wherein the linker includes a functional group selected from the group consisting of at least one of a hydrolyzable group, an amino group, at least one further silane group, an acrylate, and a methacrylate group, wherein the linker forms bonds between molecules of the alkoxysilane compound, wherein the modified inner surface forms only a partial surface area of the inner surface such that at least one unmodified partial surface remains, and wherein the at least one unmodified partial surface is bonded to a different material or has an adhesive material is applied.

* * * * *